United States Patent [19]
Kobayashi et al.

[11] Patent Number: 6,004,760
[45] Date of Patent: Dec. 21, 1999

[54] METHOD OF ASSAYING ANTIGENS RELATED TO AUTOIMMUNE DISEASES

[75] Inventors: Kensuke Kobayashi, Hiroshima; Minoru Morikawa, Shizuoka, both of Japan

[73] Assignee: Chugai Seiyaku Kabushiki Kaisha, Tokyo, Japan

[21] Appl. No.: 08/952,479

[22] PCT Filed: May 17, 1996

[86] PCT No.: PCT/JP96/01314

§ 371 Date: Jan. 28, 1998

§ 102(e) Date: Jan. 28, 1998

[87] PCT Pub. No.: WO96/36879

PCT Pub. Date: Nov. 21, 1996

[30] Foreign Application Priority Data

May 19, 1995 [JP] Japan .................................. 7-121740

[51] Int. Cl.⁶ ................................................. G01N 33/564
[52] U.S. Cl. ........................ 435/7.21; 435/7.94; 435/975; 436/506; 530/388.22; 530/389.1
[58] Field of Search ................................ 435/7.21, 7.94, 435/975; 436/506; 530/388.22, 389.1

[56] References Cited

PUBLICATIONS

Kobayashi et al., J. Immunology, vol. 143, No. 8, pp. 2567–2574 (Oct. 15, 1989).

Kobayashi et al., J. Immunology, vol. 146, No. 1, pp. 68–74 (Jan. 1, 1991).

Kobayashi et al., Digestive Diseases and Sciences, vol. 39, No. 3, pp. 526–533 (Mar. 1994).

Hamada et al., Inflammatory Bowel Diseases, vol. 2, pp. 97–104 (1996).

Hamada et al., Immunology, vol. 74, pp. 298–303 (1991).

WPAT and JAPIO Abstracts of JP 63235868.

WPAT abd JAPIO Abstracts of JP 07067689.

*Primary Examiner*—David Saunders
*Attorney, Agent, or Firm*—Birch, Stewart, Kolasch & Birch, LLP

[57] ABSTRACT

A method for immunological assay of an autoimmune disease related antigen in a human body fluid by use of antibodies to IgG Fc-binding protein, and a kit for use in this method.

17 Claims, 1 Drawing Sheet

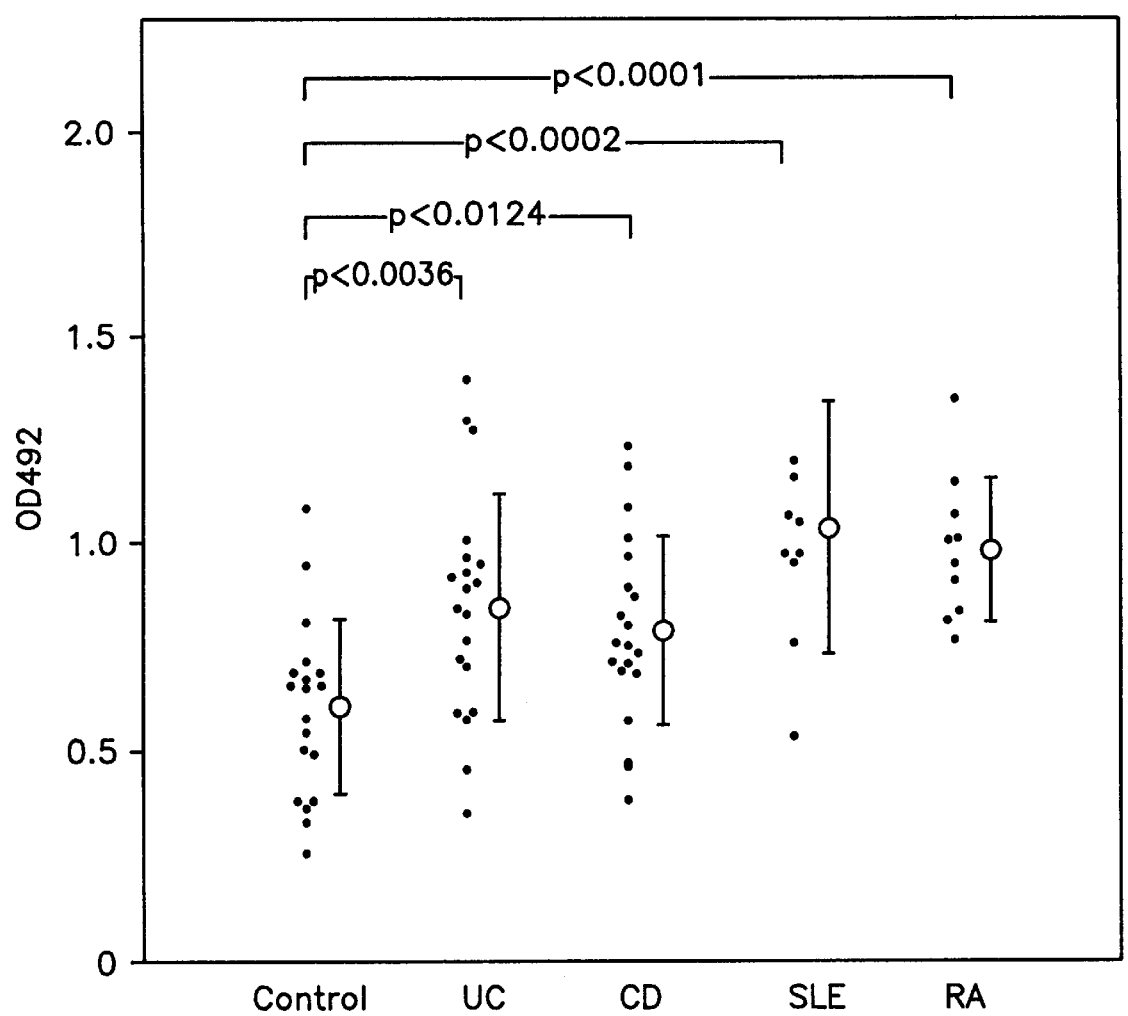

METHOD OF ASSAYING ANTIGENS RELATED TO AUTOIMMUNE DISEASES

TECHNICAL FIELD

This invention relates to the diagnosis of autoimmune disease. More specifically, it relates to a method for immunological assay of an autoimmune disease related antigen in a human body fluid by use of antibodies to IgG Fc-binding protein, and concerns a diagnostic kit for autoimmune disease which is used in this method.

BACKGROUND ART

Autoimmune disease is caused by an immune response to the antigen of one's own tissue. Alternatively, it occurs when an exogenous organism inhabiting one's body, or a product of the organism, is recognized as an antigen, and an immune response is induced to it. A hidden antigen which normally does not appear in the circulating blood, but is separated from immunocompetent cells, such as cerebral tissue, lens, thyroglobulin or sperm, may be released into the bloodstream by some trigger. Although being one's own body constituent, such a hidden antigen induces an immune response, eventually causing a pathologic state. Autoantibodies can easily develop against many intracellular constituents, but antibodies do not pass through the cell membrane, and thus do no harm to the tissue. Generally, the body is immunologically tolerant to self constituents, and undergoes no autoimmunity. Upon breakdown of immunological tolerance, however, autoantibodies may develop or cellular immunity to self may occur, causing a disease state. Many diseases have now been found to be such autoimmune diseases.

To treat autoimmune disease, corticosteroids or immunosuppressants are effective. To enhance the therapeutic effect of these drugs, early diagnosis of the disease is crucial. With ulcerative colitis or Crohn's disease, endoscopic examination is required for final diagnosis, and a simpler and safer method of diagnosis is demanded. A method by which the pathophysiology or progression of the disease can be known easily over time, if any, would be highly useful.

In autoimmune disease, production of various autoantibodies is considered an important phenomenon characterizing the disease. The mechanism which recognizes various antigens making up self's constituents and produces antibodies corresponding to them has not been thoroughly clarified yet. However, there have been attempts to use this mechanism for the diagnosis of autoimmune disease and the elucidation of its pathophysiology or etiology. Up to now, a considerable number of autoantibodies have been pointed out as having relation to particular autoimmune diseases. For the diagnosis of a certain type of autoimmune disease, screening for the corresponding autoantibodies is an inevitable test. Examples in actual practice are diagnosis of collagen disease using antinuclear antibodies, diagnosis of systemic lupus erythematosus using anti-dsDNA antibodies, diagnosis of scleroderma using autoantibodies to topoisomerase I, and diagnosis of primary biliary cirrhosis using antibodies to mitochondria-derived constituents.

The presence of IgG Fc binding protein, a protein binding specifically to the Fc region of immunoglobulin G or IgG, (FcγBP: May be described as Fcγ Binding Protein or IgGFcBP) has been reported by Kobayashi, one the present inventors, and colleagues (Kobayashi, K. et al., J. Immunol., 143:2567–2574, 1989). Specific binding of this protein to the IgG Fc region has been confirmed using a horseradish peroxidase (HRP)-labeled material. That is, FcγBP binds only to the Fc region of IgG, but does not bind to IgGFab, IgA or IgM. Nor does FcγBP cross-react with anti-Fcγ receptor :, II or III antibodies. Kobayashi et al. further partially purified FcγBP from human large intestine epithelial cells, and prepared mouse monoclonal antibodies using it as an antigen. They confirmed these antibodies to bind to mouse IgG as well as to FcγBP (Kobayashi, K. et al., J. Immunol., 143:2567–2574, 1989; Kobayashi, K. et al., J. Immunol., 146:68–74, 1991). Morikawa, one the inventors, and colleagues cloned cDNA for FcγBP with the use of monoclonal antibodies to FcγBP, and clarified the nucleotide sequence of the gene encoding FcγBP (Japanese Patent Application No. 109927/95). To date, however, no reports have boon made of the relation between FcγBP and autoimmune disease.

As described above, autoantibodies are important for the diagnosis of autoimmune diseases. However, the relationship between various autoimmune diseases and the corresponding autoantibodies is not absolute, and the antibody positive rates of these diseases are various. In some of the diseases, they are low. One kind of antibody may be detected in some diseases. Thus, to diagnose autoimmune diseases reliably, it is desirable to base their diagnosis on combinations of a plurality of autoantibodies, factors potentially regulating their amounts, and clinical findings.

DISCLOSURE OF THE INVENTION

The inventors have found that IgG FC binding protein, a protein binding specifically to the Fc region of IgG, i.e., FcγBP, is present in the sera of autoimmune disease patients in significantly large amounts, and that this protein can be detected immunologically with the use of antibodies to this protein. These findings have led them to accomplish the present invention.

That is, this invention provides a method for immunological assay of an autoimmune disease related antigen in a human body fluid by use of antibodies to IgG Fc-binding protein.

The invention also provides a diagnostic kit for autoimmune disease which contains antibodies to IgG Fc-binding protein.

BRIEF DESCRIPTION OF THE DRAWINGS

FIG. 1 shows the results of ELISA performed by the method of the present invention using sera taken from patients with various autoimmune diseases and normal human sera as control sera. In the drawing, UC stands for ulcerative colitis, CD Crohn's disease, SLE systemic lupus erythematosus, and RA rheumatoid arthritis. Each p represents a statistically significant difference between patients with each autoimmune disease and normal subjects.

BEST MODE FOR CARRYING OUT THE INVENTION

Antibodies to FcγBP for use in the present invention may be polyclonal antibodies or monoclonal antibodies. These antibodies can be produced by a method known to people skilled in the art. In the present invention, the use of monoclonal antibodies is particularly preferred. For example, K9 antibodies (deposited on May 27, 1999 pursuant to the Budapest Treaty on the International Recognition of the Deposit of Microorganisms for the Purposes of Patent Procedure, at international Depository Authority, National Institute of Bioscience and Human—Technology Agency of Industrial Science and Technology, Ministry of International Trade and Industry, Address: 1-3, Higashi 1-chome, Tsukuba-shi, Ibaraki-ken 305-8566, Japan, as FERM BP-6733) and K17 K9 antibodies (deposited on May 27, 1999 pursuant to the Budapest Treaty on the International Recognition of the Deposit of Microorganisms for the Purposes of Patent Procedure, at International Depository Authority, National Institute of Bioscience and Human—Technology agency of Industrial Science and Technology, Ministry of International Trade and Industry, Address: 1-3, Higashi 1-chome, Tsukuba-shi, Ibaraki-ken 305-8566, Japan, as FERM BP-6734) antibodies produced by Kobayashi et al. can be used.

The Immunological assay methods used in the invention may be radioimmunoassay, enzyme immunoassay, fluoroimmunoassay, luminescent immunoassay, immunosedimentation or immunonephelometry. Enzyme immunoassay, especially, ELISA (enzyme-linked immunosorbent assay) is preferred for use in hospitals and so on, since it can detect FcγBP with high sensitivity and can automatically measure many samples.

With ELISA, antibodies to FcγBP, preferably monoclonal antibodies K9 or K17 are immobilized as pray antibodies onto a carrier. A solid carrier is preferred as the carrier, and its examples include containers such as ELISA plates molded from styrene or a polymeric carrier, e.g., polystyrene. The immobilization of the monoclonal antibodies onto the carrier can be performed, for instance, by dissolving the monoclonal antibodies in a buffer solution such as carbonate buffer or borate buffer, and making the carrier adsorb the solution.

As secondary antibodies, labeled IgG, etc. can be used in addition to FcγBP-specific antibodies. FcγBP can be detected more reliably and more accurately by sandwich ELISA using monoclonal antibodies K9 or K17 as, primary antibodies and polyclonal antibodies to FcγBP as secondary antibodies, or another sandwich ELISA (to be described later on in Examples) which uses K9 antibodies as primary antibodies and HRP(horseradish peroxidase)-conjugated K17 antibodies as secondary antibodies. As the label, enzymes such as alkaline phosphatase or β-galactosidase can be used in addition to peroxidases such as HRP as described above.

An example of the standard sample is a solution (containing FcγBP) of large intestine epithelial cells prepared by the method of Kobayashi et al. (Kobayashi, K. et al., J. Immunol., 143:2567–2574, 1989).

Body fluids that can be used in the present invention are blood components such as serum or plasma, lymph, and synovial fluid. Particularly preferred are blood components, especially serum, taken from patients suspected of having autoimmune diseases.

Autoimmune diseases that can be detected by the method of the invention include ulcerative colitis, Crohn's disease, systemic lupus erythematosus, and rheumatoid arthritis. However, they are not restricted to these diseases, and any autoimmune diseases which involve FcγBP can be likewise subjected to the method of the present invention.

The present invention further provides a diagnostic kit for autoimmune disease which contains antibodies to IgG Fc-binding protein. This kit, if it uses two kinds of monoclonal antibodies, for example, contains a carrier on which monoclonal antibodies of one kind against FcγBP have been immobilized, or monoclonal antibodies to FcγBP and a carrier for immobilizing them, and another kind of labeled monoclonal antibodies. Thin kit may further have a standard curve, an instruction manual on a standard solution of FcγBP, and so forth.

The amounts of FcγBP in the sera of patients with ulcerative colitis, Crohn's disease, systemic lupus erythematosus, and rheumatoid arthritis were measured by the method of the present invention, and compared with those in normal subjects. Statistically significant differences were observed between the normal group and the group with any autoimmune disease. This result shows that the method of the invention can be used to diagnose autoimmune diseases and monitor changes in the pathological state over time.

Thus, the method and kit of the present invention enable an autoimmune disease related antigen to be measured briefly and highly accurately. Combining the method of the invention with an immunological method using other antibodies to an autoimmune disease related antigen. or with clinical findings, makes it possible to diagnose autoimmune diseases easily.

EXAMPLE

The present invention will be described concretely by the following Examples, but the scope of the invention is not limited thereto:

Example 1

Assay of FcγBP by sandwich ELISA

K9 antibodies prepared by the method of Kobayashi et al. (Kobayashi, K. et al., J. Immunol., 146:68–74, 1991) were affinity purified, and adjusted with 0.05 M carbonate buffer (pH 9.2) to 5 μg/ml. This material was added to an ELISA plate (PRO-BIND, Falcon) at 50 μl/well, and allowed to stand overnight at 4° C. The wells were washed with a washing solution (PBS(-) containing 0.05% Tween-20) three times. Then, a blocking solution (RPMI1640 medium containing 10% serum) wax added in an amount of 50 μl/well, and the mixture was allowed to stand for 60 minutes at room temperature. The blocking solution was removed, and various dilutions of the aforementioned standard sample were each added in an amount of 50 μl , whereafter the mixtures were allowed to stand for 2 hours at room temperature. The wells were washed 3 times with the washing solution, and diluted to 4 mg/ml with the blocking solution.

Then, HRP-conjugated K17 antibodies (prepared by the method described in Kobayashi, K. et al., J. Immunol., 143:2567–2574, 1989; K17 antibodies were prepared by the method described in the aforementioned Kobayashi, K. et al., J. Immunol., 146:68–74, 1991) were added in an amount of 50 μl, whereafter the mixtures were allowed to stand for 1 hour at room temperature. After the system was washed 3 times with the washing solution. 50 μl of a color developing solution (a solution of 20 mg o-phenylenediamine and 80 μl $H_2O_2$ (30%) in 50 ml of citrate buffer) was added to cause color development for 30 minutes at room temperature. A 2.5 M $H_2SO_4$ solution (50 μl) was added to stop the reaction. Then, the absorbance at 492 nm was measured. The results are shown in Table 1.

TABLE 1

| Sample | | $OD_{492}$ |
| --- | --- | --- |
| Solution of large intestine epithelial cells | 1:100 dilution | 2.184 |
| | 1:200 dilution | 2.024 |
| | 1:400 dilution | 1.516 |
| | 1:800 dilution | 0.935 |
| | 1:1600 dilution | 0.514 |
| | 1:3200 dilution | 0.264 |

According to the ELISA of the present invention, the absorbance varied with the degree of dilution of the standard sample containing FcγBP, and a very high linear relationship was obtained between the degree of dilution of the solution of large intestine epithelial cells and the absorbance at 492 nm. Thus, the content of FcγBP in the sample can be read highly accurately from the measurements of absorbance by ELISA. Based on the readings, a standard curve was plotted, and used for the determination of FcγBP in human serum.

Example 2

Determination of FcγBP in human serum

The antigen levels of FcγBP in the sera of patients with autoimmune diseases were measured to screen for various autoimmune diseases or evaluate the state of the disease. The diseases ware ulcerative colitis (UC; 20 patients), Crohn's disease (CD; 20 patients), systemic lupus erythematosus (SLE; 10 patients), and rheumatoid arthritis (RA; 10 patients) which are classified as autoimmune diseases. The same tests ware conducted in normal individuals (20 people) as a control group.

About 5 ml of blood was taken from each patient, and allowed to stand for 0.5 to 1.0 hour on ice (4° C.). Then, the blood was centrifuged for 15 minutes at 1,000 rpm, and the supernatant was collected for use as a serum sample. The serum samples thus obtained were stored at −30° C.

Each serum sample (50 μl) was transferred into each of the three wells of the same ELISA plate as prepared by the method of Example 1. The FcγBP antigen level in the serum was measured by the method described in Example 1.

The results obtained are shown in FIG. 1. Each dot in the drawing is the average of three measured values. Based on these results, statistical analysis was made by t-test to calculate significant differences (p) from the results in the control group. As shown in FIG. 1, significant differences were observed between the patient group and the control group in any of the diseases, UC, CD, SLE and RA. Hence, a strong correlation was noted between these diseases and the FcγBP antigen level in serum. This finding suggested the assay method of the present invention to be usable for the diagnosis of these autoimmune diseases.

We claim:

1. A method for immunological assay of an autoimmune disease related antigen in a human body fluid, comprising:

contacting a sample comprising said human body fluid, said human body fluid containing IgG Fc-binding protein, with antibodies to IgG Fc-binding protein of human large intestine epithelial cells; and detecting the antibody-protein complex.

2. The method of claim 1, wherein the antibodies to IgG Fc-binding protein are monoclonal antibodies.

3. The method of claim 2, wherein the monoclonal antibodies are selected from the group consisting of K9 antibodies (FERM BP-6733) and K17 antibodies (FERM BP-6734).

4. The method of claim 1, wherein the immunological assay is ELISA.

5. The method of claim 1, wherein the body fluid is a blood component.

6. The method of claim 5, wherein the blood component is serum.

7. The method of claim 1, wherein the autoimmune disease is ulcerative colitis .

8. The method of claim 1, wherein the autoimmune disease in Crohn's disease.

9. The method of claim 1, wherein the autoimmune disease is systemic lupus erythematosus.

10. The method of claim 1, wherein the autoimmune disease is rheumatoid arthritis.

11. A diagnostic kit for autoimmune disease, comprising:

primary antibodies to IgG Fc-binding protein immobilized on a carrier or primary antibodies to IgG Fc-binding protein of human large intestine epithelial cells and a carrier for immobilizing said primary antibodies; and labeled secondary antibodies to IgG Fc-binding protein of human large intestine epithelial cells.

12. The diagnostic kit for autoimmune disease of claim 11, wherein said primary antibodies are monoclonal.

13. The diagnostic kit for autoimmune disease of claim 12, wherein said primary antibodies are selected from the group consisting of K9 antibodies (FERM BP-6733) and K17 antibodies (FERM BP-6734).

14. The diagnostic kit for autoimmune disease of claim 11, wherein said secondary antibodies are polyclonal.

15. The diagnostic kit for autoimmune disease of claim 11, wherein said primary antibodies are K9 antibodies (FERM BP-6733) and said secondary antibodies are labeled K17 antibodies (FERM BP-6734).

16. The diagnostic kit for autoimmune disease of claim 11, wherein said carrier is a solid carrier.

17. The diagnostic kit for autoimmune disease of claim 11, further comprising a standard curve, an instructional manual or a standard solution of IgG Fc-binding protein.

* * * * *